(12) United States Patent
Mashford et al.

(10) Patent No.: US 11,013,417 B2
(45) Date of Patent: May 25, 2021

(54) ENERGY-EFFICIENT MULTISENSORY SYSTEM FOR MOBILE HEALTH-MONITORING

(71) Applicant: International Business Machines Corporation, Armonk, NY (US)

(72) Inventors: Benjamin Scott Mashford, Southbank (AU); Mahtab Mirmomeni, Melbourne (AU); Subhrajit Roy, Melbourne (AU); Filiz Isabell Kiral-Kornek, Southbank (AU); Stefan Harrer, Melbourne (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 129 days.

(21) Appl. No.: 16/160,063

(22) Filed: Oct. 15, 2018

(65) Prior Publication Data
US 2020/0113444 A1    Apr. 16, 2020

(51) Int. Cl.
*A61B 5/0205* (2006.01)
*A61B 5/00* (2006.01)
*G16H 10/60* (2018.01)

(52) U.S. Cl.
CPC .......... *A61B 5/0205* (2013.01); *A61B 5/0006* (2013.01); *A61B 5/6802* (2013.01); *A61B 5/7282* (2013.01); *A61B 5/6898* (2013.01); *A61B 2560/0209* (2013.01); *A61B 2560/0214* (2013.01); *A61B 2562/0219* (2013.01); *A61B 2562/0271* (2013.01); *G16H 10/60* (2018.01)

(58) Field of Classification Search
CPC .... A61B 2560/0209; A61B 2560/0214; A61B 2562/0219; A61B 2562/0271; A61B 5/0006; A61B 5/0205; A61B 5/6802; A61B 5/6898; A61B 5/7282; G16H 10/60; G04G 21/00–21/025
USPC ....................................... 361/679.01–679.03
See application file for complete search history.

(56) References Cited

U.S. PATENT DOCUMENTS

| | | | |
|---|---|---|---|
| 8,862,215 B2 * | 10/2014 | Puolakanaho | A61B 5/0002 600/520 |
| 9,946,571 B1 | 4/2018 | Brown et al. | |
| 2014/0107501 A1 | 4/2014 | Komanduri et al. | |

(Continued)

FOREIGN PATENT DOCUMENTS

EP    3 061 390 A1    8/2016

OTHER PUBLICATIONS

Mel, et al. "The NIST Definition of Cloud Computing". Recommendations of the National Institute of Standards and Technology. Nov. 16, 2015.

(Continued)

*Primary Examiner* — Jonathan T Kuo
(74) *Attorney, Agent, or Firm* — Joseph Petrokaitis, Esq.; McGinn I.P. Law Group, PLLC

(57) ABSTRACT

A health-monitoring method, system, and computer program product include operating at least one sensor of a health-monitoring device having a plurality of sensors, detecting a health condition event that requires operation of an additional sensor of the plurality of sensors to monitor the health condition event, activating the additional sensor of the health-monitoring device, and deactivating the additional sensor when the health condition event that requires the second sensor is no longer detected by the detecting.

17 Claims, 6 Drawing Sheets

(56) References Cited

U.S. PATENT DOCUMENTS

| | | | |
|---|---|---|---|
| 2014/0200470 A1* | 7/2014 | Puolakanaho | G06F 19/3481 |
| | | | 600/509 |
| 2015/0181087 A1 | 6/2015 | Mistry et al. | |
| 2017/0039480 A1 | 2/2017 | Bitran et al. | |
| 2018/0140254 A1 | 5/2018 | Kubo et al. | |
| 2018/0263538 A1* | 9/2018 | Heikenfeld | A61B 5/6843 |

OTHER PUBLICATIONS

Womjun Lee, "Ultra-low-power Pulse Oximeter with a 32.768 kHZ Real Clock" IDIE Transactions on Smart Processing and Computing, vol. 6, No. 2, Apr. 2017, pp. 129-132.

* cited by examiner

ENERGY-EFFICIENT MULTISENSORY SYSTEM FOR MOBILE HEALTH-MONITORING

BACKGROUND

The present invention relates generally to a health-monitoring method, and more particularly, but not by way of limitation, to a system, method, and computer program product to run a decision tree that is designed to optimize overall performance by considering the energy consumption of analyzing each data modality for health-monitoring.

Portable electronic devices contain a variety of sensor and information processing units. These components can capture and analyze a wide range of sensory inputs (e.g., motion, skin conductance, audio, video, etc.).

Conventionally, there is a trade-off between the quantity of analyzed input data and power consumption. A highest accuracy may be obtained by operating all of the components in a continuous manner, but this will drain battery life quickly. Modern wearable devices contain multiple processors that offer varying levels of performance and power consumption.

One conventional technique considers a self-powered (e.g., powered via a solar panel) sensing device that contains a logic unit that enable it to switch between different operating modes based on available power and tasks needed. However, this technique does not consider a wearable device for classifying multimodal healthcare signals, where sensors and on-board processors are switched on/off based on a confidence of event detection.

SUMMARY

In an exemplary embodiment, the present invention provides a computer-implemented health-monitoring method, the method including operating at least one sensor of a health-monitoring device having a plurality of sensors, detecting a health condition event that requires operation of an additional sensor of the plurality of sensors to monitor the health condition event, activating the additional sensor of the health-monitoring device, and deactivating the additional sensor when the health condition event that requires the second sensor is no longer detected by the detecting. One or more other exemplary embodiments include a computer program product and a system, based on the method described above.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

Figure 1:
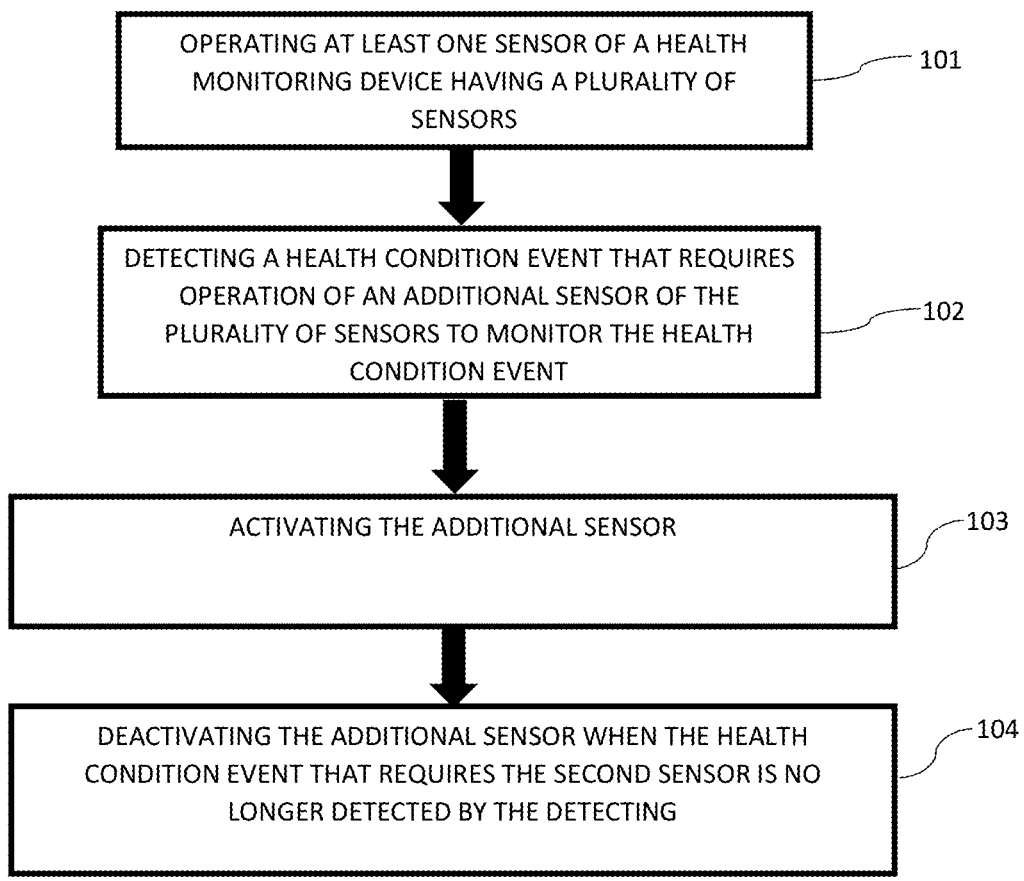
FIG. 1 exemplarily shows a high-level flow chart for a health-monitoring method 100 according to an embodiment of the present invention.

The invention will now be described with reference to FIGS. 1-6, in which like reference numerals refer to like parts throughout. It is emphasized that, according to common practice, the various features of the drawing are not necessarily to scale. On the contrary, the dimensions of the various features can be arbitrarily expanded or reduced for clarity.

By way of introduction of the example depicted in FIG. 1, an embodiment of a health-monitoring method 100 according to the present invention can include various steps for operating a wearable healthcare device that contains multiple processors and wireless communication options. The device handles multiple input streams (modalities) and dynamically re-configures its operation based upon the power available in the device battery. The analysis pipeline is configured to maximize analysis accuracy while minimizing power consumption.

Thus, the invention runs a decision tree that is designed to optimize overall performance by considering the energy consumption of analyzing each data modality.

Figure 4:
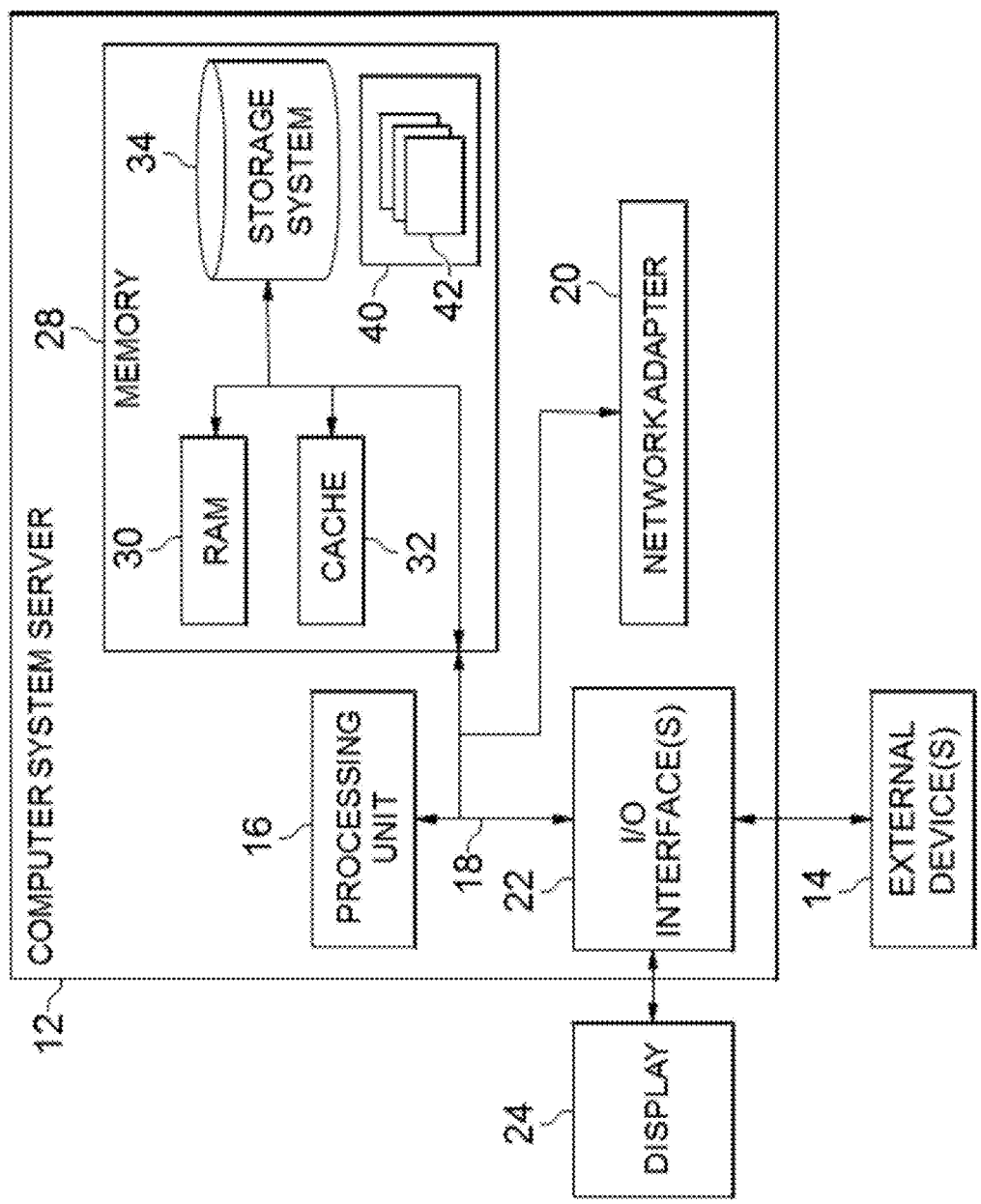
FIG. 4 depicts a cloud-computing node 10 according to an embodiment of the present invention.

By way of introduction of the example depicted in FIG. 4, one or more computers of a computer system 12 according to an embodiment of the present invention can include a memory 28 having instructions stored in a storage system to perform the steps of FIG. 1.

Although one or more embodiments may be implemented in a cloud environment 50 (e.g., FIG. 6), it is nonetheless understood that the present invention can be implemented outside of the cloud environment.

Referring to FIG. 1, in step 101, at least one sensor of a health-monitoring device is operated having a plurality of sensors. That is, input signal streams of a health-monitoring device are captured simultaneously from various sensors when they are operated (e.g. EEG EMG ECG accelerometer, audio, video, etc.). Sensors may reside on single device or across multiple networked devices, (e.g. a fitness wearable and glucose monitoring wearable connected via Bluetooth to smartphone). Depending on situation, signal analysis may be done locally (e.g. on smartphone, or on the cloud). For example, a health-monitoring device can have five sensors. At least one of the five sensors is operated (e.g., active) in step 101 to collet health care data of a person. The other four sensors remain off (e.g., inactive).

In step 102, a health condition event that requires operation of an additional sensor of the plurality of sensors is detected to monitor the health condition event. For example, if the sensor currently active is monitoring a temperature of a person and a health condition occurs where a heart rate monitor is required, step 102 detects the health condition that cannot be tracked by the current sensor and that requires an additional sensor to be activated.

In step 103, the additional sensor for monitoring the health condition event is activated. That is, a sensor that is currently off is turned on (e.g., a power consumption of the additional sensor is active) such that the sensor consumes power of the health-monitoring device.

In step 104, the additional sensor is deactivated (e.g., a power consumption is turned off) when the health condition event that requires the second sensor is no longer detected by the detecting (e.g., step 102). In other words, when the health condition event subsides, the additional sensor is no longer required to be active and is subsequently deactivated to reduce a power consumption of the health-monitoring device.

Figure 2:
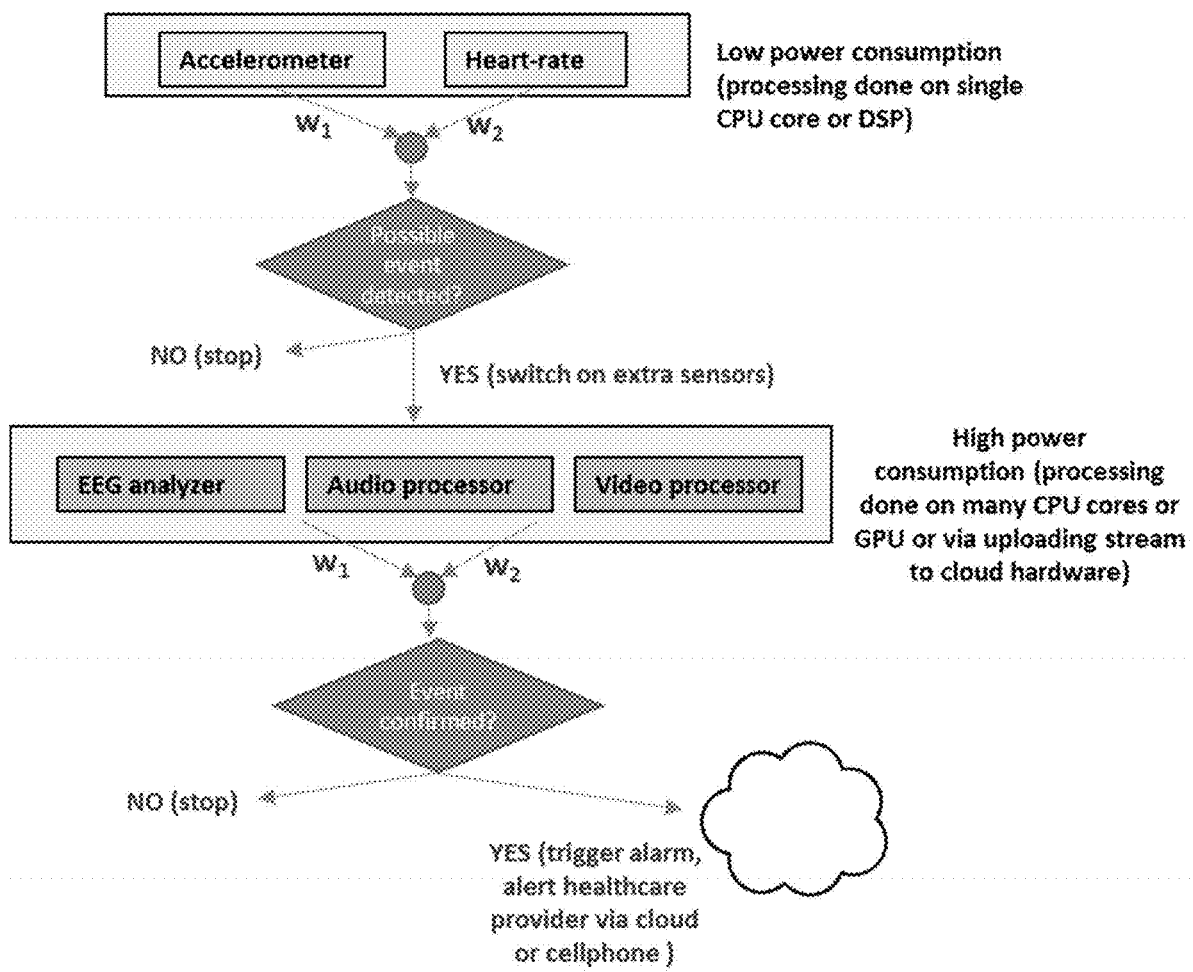
FIG. 2 exemplarily depicts an exemplary decision tree according to an embodiment of the present invention.
Figure 3:
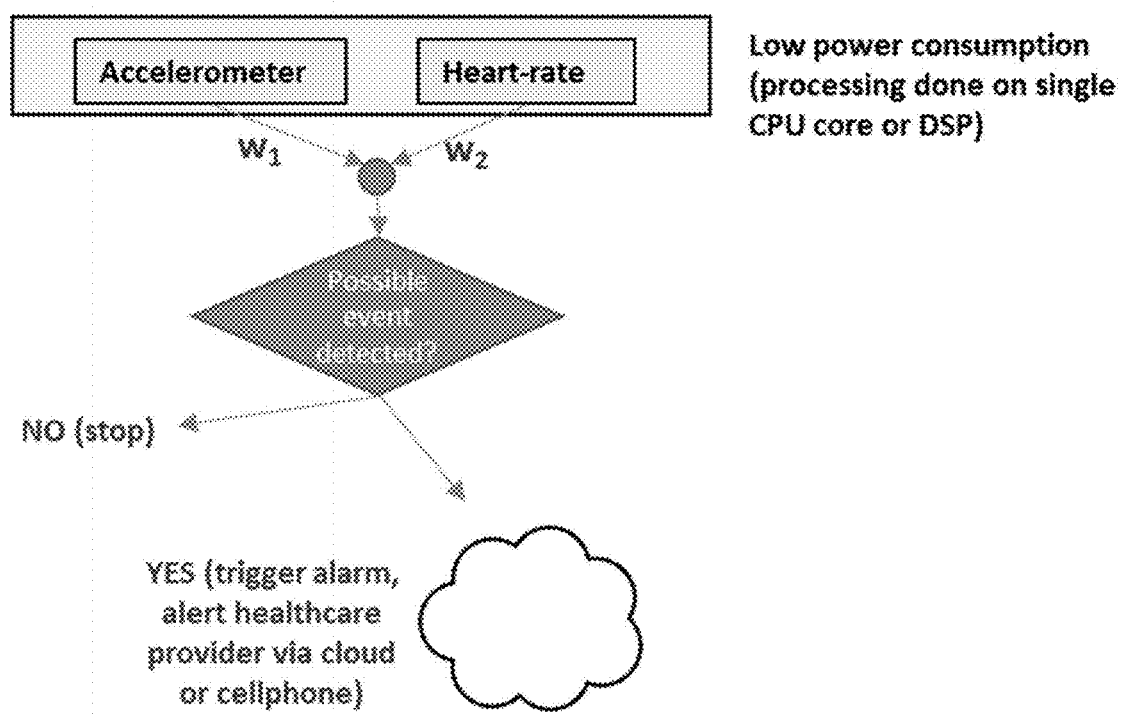
FIG. 3 exemplarily depicts an exemplary decision tree for a low power mode according to an embodiment of the present invention.

The method 100 runs a decision tree (e.g., as depicted in FIGS. 2-3) to determine when to activate and deactivate sensors that is designed to optimize overall performance by considering the energy consumption of analyzing each data modality. For instance, analyzing heart-rate signal will be less computationally (and power) expensive than EEG or video data, so the method can monitor heart-rate continuously and only switch on other signal analysis when a possible event is detected. The decision tree is trainable via weights that are set automatically. Or, the weights can be learned.

For example, a weight can be associated with an importance of activating the additional sensors versus a weight of the importance of the health condition and a weight of a time left on the battery power of the health-monitoring device. In one embodiment, if the weight of importance is low (e.g., the health condition is not important to require the sensor), and the battery is also low in battery life, the sensor will be ignored. However, in another embodiment, even if the battery life is low, if a health condition event is very important (e.g., high weight of importance as such is life-threatening), the additional sensor is turned on since the weight outweighs the battery life importance.

The analysis pipeline will progress to the next level in the decision tree after a particular confidence threshold is exceeded. For example, once the health condition event is detected and a weight of the health condition event exceeds a threshold, the method will proceed to activate the additional sensor (e.g., a video recording will not be activated unless the health condition event exceeds a threshold weight).

Referring now to FIGS. 2-3, in FIG. 2, an exemplary decision tree is depicted. In a low power consumption mode (e.g., step 101), sensors are operated that require little operating power (e.g., a power consumption of the sensors is low). If an event is detected (e.g., "YES"), then additional sensors are activated (e.g., steps 102-103). Then, the sensors are monitored while they are active to determine when a weight of the active sensors decreases below a threshold value such that the sensors can safely be deactivated (e.g., the health condition event has passed).

Also, in one embodiment, the sensors can be activated until the health condition event is confirmed. That is, the sensors will be active until the event is confirmed. If the event is confirmed as being important, then a trigger is set off and a health care professional is contacted. If the event subsides or is a false alarm, then the sensors can be deactivated. Or, if the sensors take a reading and the reading provides a positive result (e.g., no health risk), then the sensors can be deactivated in step 104.

The decision made at each branch of the tree will also include the total power left in the device battery. If the battery is full, then the likelihood to turn on extra sensors will be higher than if the battery level is running low. The method is tuned such that the 'low battery level mode' has high sensitivity but low specificity (high false positive rate) while the 'high battery level mode' has both high sensitivity and specificity. In this way, no relevant events are missed.

Referring now to FIG. 3, FIG. 3 exemplarily depicts a low power mode in which a health care professional or an alarm is triggered instead of an actual sensor being activated. That is, the additional sensor being activated notifies a health care professional. This mode can be active when the battery life is less than a threshold value (e.g., 20% battery life) such that the current active sensors can continue to monitor the health of the patient without an additional sensor potentially jeopardizing the battery life by more quickly depleting the battery life. In this embodiment, the health care professional can be contacted to replace the battery.

In a preferred embodiment, as depicted in FIG. 2, the activating activates additional sensors that are "high power" sensors (e.g., require large amounts of battery consumption) to confirm whether or not the event is occurring. That is, the additional sensors act as a fail safe check to determine whether or not the health condition is occurring. If the event is occurring, then a health care professional can be contacted. For example, an accelerometer and a heart-rate sensor can be continuously active (e.g., the at least one sensor) when they detect the possible health condition event of an epileptic seizure. To confirm whether the person is having a seizure, a video processor is turned on (e.g., additional sensor) to view whether the patient is having the seizure. Because of the importance of monitoring a seizure, regardless of battery power (e.g., high weights), the video processor is always turned on to be cautious and confirm whether the patient is having a seizure. If the patient is not having the seizure, then the additional sensor is deactivated to reduce battery consumption. And, if they are having a seizure, a health care professional can be contacted. Therefore, the invention not only saves battery consumption for a health care device but also provides better medical care for patients with less sensors being active (e.g., less sensors typically means the patient is more comfortable).

Preferably, the sensors always active are relatively lower power consumption sensors and the additional sensors are relatively high power sensors with higher accuracy to confirm a health condition possibly detected by the low power sensors.

Thus, the invention described herein includes a new wearable healthcare device that contains multiple processors and wireless communication options. The device handles multiple input streams (modalities) and dynamically re-configures its operation based upon the power available in the device battery. The analysis pipeline is configured to maximize analysis accuracy while minimizing power consumption.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
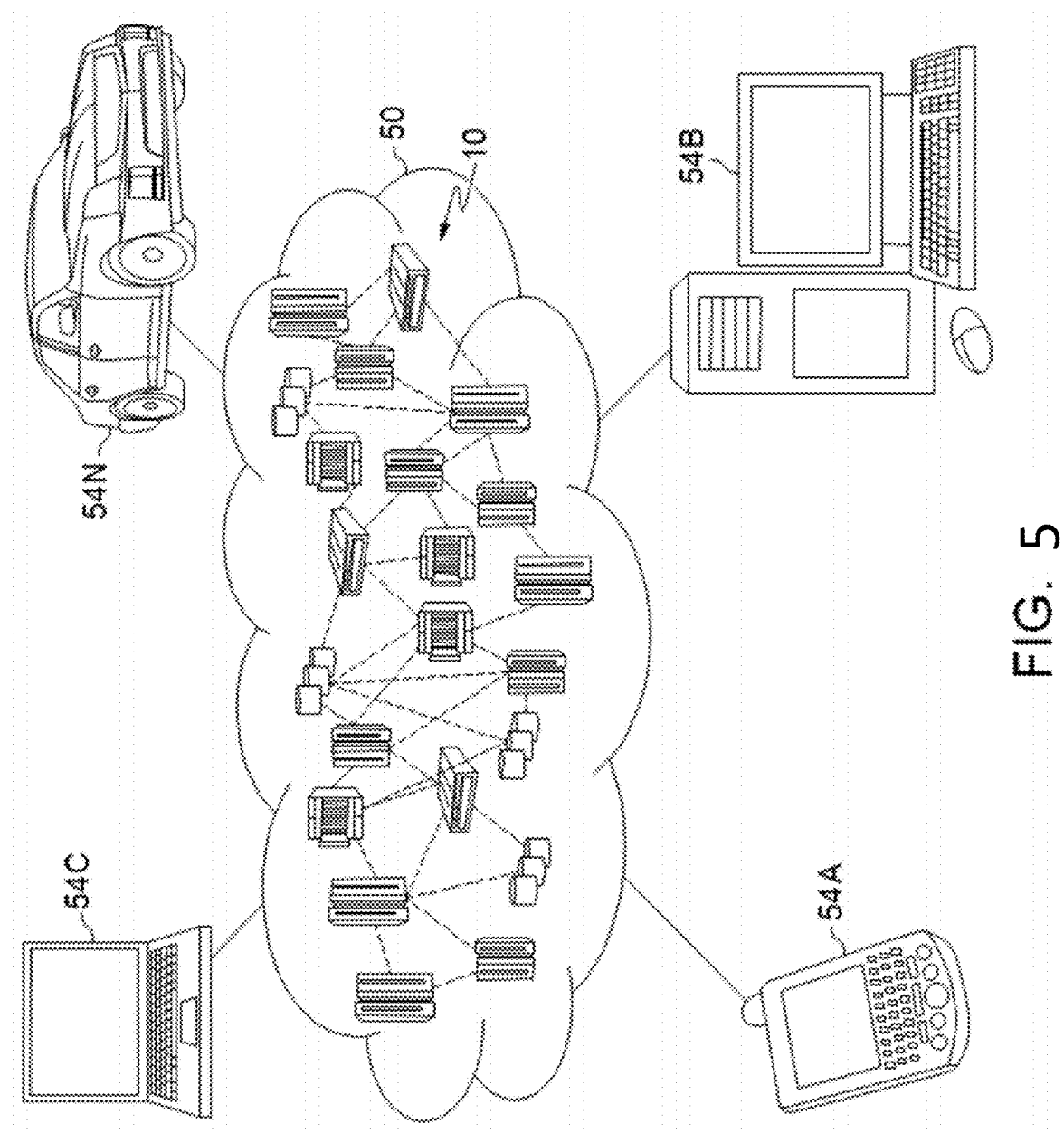
FIG. 5 depicts a cloud-computing environment 50 according to an embodiment of the present invention.

Referring now to FIG. 5, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring now to FIG. 5, a computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further described below, memory 28 may include a computer program product storing one or more program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may be adapted for implementation in a networking environment. In some embodiments, program modules 42 are adapted to generally carry out one or more functions and/or methodologies of the present invention.

Computer system/server 12 may also communicate with one or more external devices 14 such as a keyboard, a pointing circuit, other peripherals, such as display 24, etc., and one or more components that facilitate interaction with computer system/server 12. Such communication can occur via Input/Output (I/O) interface 22, and/or any circuits (e.g., network card, modem, etc.) that enable computer system/server 12 to communicate with one or more other computing circuits. For example, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 6:
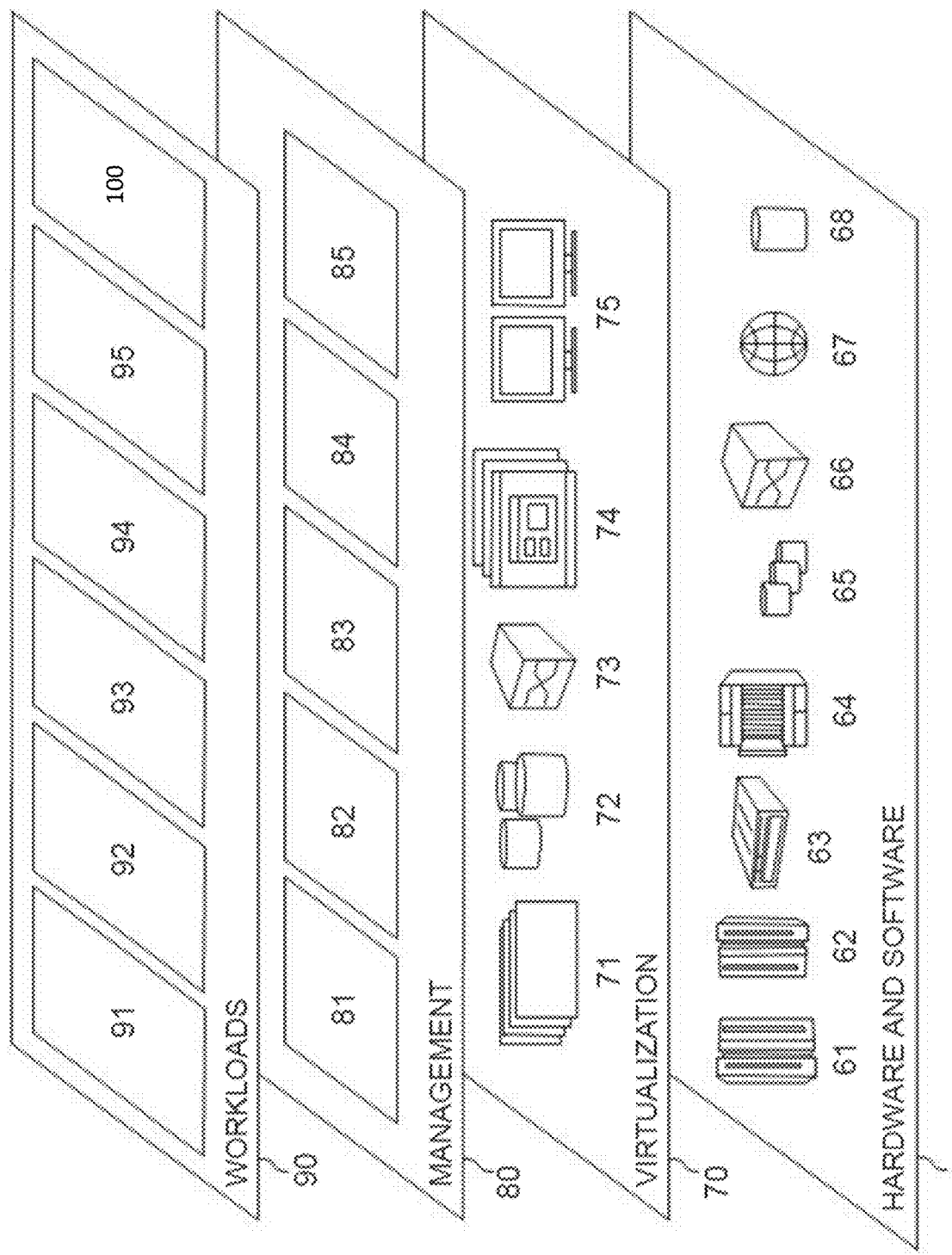
FIG. 6 depicts abstraction model layers according to an embodiment of the present invention.

Referring now to FIG. 6, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 6 are intended to be illustrative only and that computing nodes 10 and cloud computing environment 50 can communicate with any type of computerized circuit over any type of network and/or network addressable connection (e.g., using a web browser).

Referring now to FIG. 7, an exemplary set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91;

software development and lifecycle management 92; virtual classroom education delivery 93; data analytics processing 94; transaction processing 95; and health-monitoring method 100 in accordance with the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented health-monitoring method, the method comprising:
   operating at least one sensor of a health-monitoring device having a plurality of sensors;
   detecting a health condition event having a different health condition that requires operation of an additional sensor that is not active and that is a different sensor with a different measuring capability for monitoring a symptom associated with the health condition event than the at least one sensor of the plurality of sensors to monitor the health condition event that is already active;
   activating the additional sensor of the health-monitoring device to monitor the different health condition using the different measuring capability of the additional sensor based on a result of the detecting; and
   deactivating one of the activated sensors when a confidence value that the health condition event that requires the one of the activated sensors is no longer detected by the detecting is greater than a predetermined confidence value,
   wherein the health-monitoring device comprises a wearable device for performing classification of streaming multi-modal data, and
   wherein the activating only activates the additional sensor when a power supply of the health-monitoring device is greater than a predetermined threshold value,
   further comprising running a decision tree to determine when to activate and deactivate the additional sensor, the decision tree being configured to optimize overall performance by considering an energy consumption of utilizing the different measuring capability.

2. The computer-implemented method of claim 1, wherein a power consumption of the at least one sensor being operated is less than a predetermined threshold value, and
   wherein the different measuring capability includes measuring the different health condition by using a different type of measurement than the sensor.

3. The computer-implemented method of claim 1, wherein a power consumption of the at least one sensor being operated is less than a power consumption of the additional sensor.

4. The computer-implemented method of claim 1, wherein the additional sensor measures a signal output from the health condition event.

5. The computer-implemented method of claim 1, wherein the at least one sensor of the health-monitoring device having the plurality of sensors and the additional sensor of the health-monitoring device having the plurality of sensors are activated on a second health-monitoring device.

6. The computer-implemented method of claim 1, wherein the activating turns on a power consumption of the additional sensor, and
   wherein the deactivating turns off the power consumption of the additional sensor.

7. The computer-implemented method of claim 1, wherein the detecting determines a weight of importance associated with the health condition event and a weight associated with a time left of a battery life of the health-monitoring device if the additional sensor is activated, and
   wherein the activating only activates the additional sensor when the weight of importance associated with the health condition event is greater than the weight associated with the time left of the battery life of the health-monitoring device.

8. The computer-implemented method of claim 1, embodied in a cloud-computing environment.

9. A computer program product for health-monitoring, the computer program product comprising a computer-readable storage medium having program instructions embodied therewith, the program instructions executable by a computer to cause the computer to perform:
   operating at least one sensor of a health-monitoring device having a plurality of sensors;
   detecting a health condition event having a different health condition that requires operation of an additional sensor that is not active and that is a different sensor with a different measuring capability for monitoring a symptom associated with the health condition event than the at least one sensor of the plurality of sensors to monitor the health condition event that is already active;
   activating the additional sensor of the health-monitoring device to monitor the different health condition using the different measuring capability of the additional sensor based on a result of the detecting; and
   deactivating one of the activated sensors when a confidence value that the health condition event that requires the one of the activated sensors is no longer detected by the detecting is greater than a predetermined confidence value,
   wherein the health-monitoring device comprises a wearable device for performing classification of streaming multi-modal data, and
   wherein the activating only activates the additional sensor when a power supply of the health-monitoring device is greater than a predetermined threshold value,
   further comprising running a decision tree to determine when to activate and deactivate the additional sensor, the decision tree being configured to optimize overall performance by considering an energy consumption of utilizing the different measuring capability.

10. The computer program product of claim 9, wherein a power consumption of the at least one sensor being operated is less than a predetermined threshold value.

11. The computer program product of claim 9, wherein a power consumption of the at least one sensor being operated is less than a power consumption of the additional sensor.

12. The computer program product of claim 9, wherein the additional sensor measures a signal output from the health condition event.

13. The computer program product of claim 9, wherein the at least one sensor of the health-monitoring device having the plurality of sensors and the additional sensor of the health-monitoring device having the plurality of sensors are activated on a second health-monitoring device.

14. The computer program product of claim 9, wherein the activating turns on a power consumption of the additional sensor, and
wherein the deactivating turns off the power consumption of the additional sensor.

15. A health-monitoring system, the system comprising:
a health-monitoring device;
a processor; and
a memory, the memory storing instructions to cause the processor to perform:
   operating at least one sensor of a health-monitoring device having a plurality of sensors;
   detecting a health condition event having a different health condition that requires operation of an additional sensor that is not active and that is a different sensor with a different measuring capability for monitoring a symptom associated with the health condition event than the at least one sensor of the plurality of sensors to monitor the health condition event that is already active;
   activating the additional sensor of the health-monitoring device to monitor the different health condition using the different measuring capability of the additional sensor based on a result of the detecting; and
   deactivating one of the activated sensors when a confidence value that the health condition event that requires the one of the activated sensors is no longer detected by the detecting is greater than a predetermined confidence value,
wherein the health-monitoring device comprises a wearable device for performing classification of streaming multi-modal data, and
wherein the activating only activates the additional sensor when a power supply of the health-monitoring device is greater than a predetermined threshold value,
further comprising running a decision tree to determine when to activate and deactivate the additional sensor, the decision tree being configured to optimize overall performance by considering an energy consumption of utilizing the different measuring capability.

16. The system of claim 15, embodied in a cloud-computing environment.

17. The system of claim 15, wherein the different measuring capability includes measuring the different health condition by using a different type of measurement than the sensor.

* * * * *